United States Patent
Duval (10) Patent No.: US 8,347,757 B2
(45) Date of Patent: *Jan. 8, 2013

(54) METHOD AND APPARATUS FOR REDUCING AT LEAST ONE FRICTION FORCE OPPOSING AN AXIAL FORCE EXERTED THROUGH AN ACTUATOR ELEMENT

(75) Inventor: Eugene F. Duval, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/425,623

(22) Filed: Mar. 21, 2012

(65) Prior Publication Data

US 2012/0174694 A1    Jul. 12, 2012

Related U.S. Application Data (63) Continuation of application No. 12/340,875, filed on Dec. 22, 2008, now Pat. No. 8,161,838.

(51) Int. Cl.
*B25J 17/00* (2006.01)
*A61B 17/00* (2006.01)

(52) U.S. Cl. .......................... 74/490.04; 606/1

(58) Field of Classification Search ............... 74/490.04, 74/469, 479, 490.01, 490.05, 479.01; 606/114, 606/120, 143, 146, 151, 101–109, 1; 604/510; 700/250, 258

See application file for complete search history.

(56) References Cited

U.S. PATENT DOCUMENTS

| | | |
|---|---|---|
| 3,901,425 A | 8/1975 | Taylor et al. |
| 4,646,736 A | 3/1987 | Auth |
| 5,242,441 A | 9/1993 | Avitall |
| 5,512,044 A | 4/1996 | Duer |
| 6,371,952 B1 | 4/2002 | Madhani et al. |
| 6,398,190 B1 | 6/2002 | Li |
| 6,699,235 B2 | 3/2004 | Wallace et al. |
| 6,817,974 B2 | 11/2004 | Cooper et al. |
| 6,974,449 B2 | 12/2005 | Niemeyer |
| 7,090,683 B2 | 8/2006 | Brock et al. |
| 7,806,892 B2 | 10/2010 | Makin et al. |
| 2004/0138700 A1 | 7/2004 | Cooper et al. |
| 2007/0197939 A1 | 8/2007 | Wallace et al. |
| 2007/0233044 A1 | 10/2007 | Wallace et al. |

OTHER PUBLICATIONS

Vertut, Jean and Phillipe Coiffet, *Robot Technology: Teleoperation and Robotics Evolution and Development*, Prentice-Hall, Inc., Inglewood Cliffs, NJ, USA 1986, vol. 3A, 332 pages.

*Primary Examiner* — Robert Pezzuto (57) ABSTRACT

Actuator elements such as cables or push rods in an instrument are used for manipulating an end effector or distal end of the instrument. Each actuator element extends within a tubular housing and either the tubular housing is axially rotated about the actuator element or the actuator element is axially rotated within the tubular housing to reduce at least one force opposing an axial force exerted through or movement of the actuator element.

17 Claims, 8 Drawing Sheets fig.1 fig.2 fig.3 fig.4 fig.5 fig.6a fig.6b fig.7 fig.8 fig.9 fig.10 ment.
METHOD AND APPARATUS FOR REDUCING AT LEAST ONE FRICTION FORCE OPPOSING AN AXIAL FORCE EXERTED THROUGH AN ACTUATOR ELEMENT This application is a continuation of U.S. patent application No. 12/340,875 (filed on Dec. 22, 2008) now U.S. Pat. No. 8,161,838.

FIELD OF THE INVENTION

The present invention generally relates to the reduction of friction in mechanical devices and in particular, to a method and apparatus for reducing at least one friction force opposing an axial force exerted through an actuator element.

BACKGROUND OF THE INVENTION

Friction can be detrimental to the performance and operation of mechanical devices. An instrument (such as a medical device) that includes a movable actuator element (such as a pull cable or push rod) to operate an end effector (such as a grasper or scissor) of the instrument may experience considerable friction forces detrimental to its performance and operation. Controlling both static and dynamic friction is important. For example, negative slopes on the force vs. velocity curve (such as caused by static friction) are undesirable since they may lead to jerky stick-slip motion.

Also, sliding friction that results from the actuator element sliding over (or otherwise having physical contact with) other surfaces as it moves to actuate the end effector can result in significant loss of force transmission which reduces the available force to the end effector, thus adversely affecting its use. In particular, such force transmission loss means that more force must be exerted at an input end of the instrument (either manually for hand operated instruments or by an actuator that actuates the actuator element) to generate a desired force at the end effector. Thus, it becomes harder to exert the desired force to grasp or cut something using the end effector.

Accuracy of the force transmission is also important. As an example, assume that for continuous cable motion, only half the force applied to the proximal end of a cable reaches the distal end. In many applications, most of the cable motion will not be continuous or steady state. The cable motion will be intermittent, back and forth in both directions. As a result, if the applied force is known only at the proximal end, the force at the distal end may be any value between one half the proximal force to two times the proximal force. Thus, if the transmitted force is being used to tension a suture, the suture may be anywhere between only half as tight as intended and twice as tight as intended.

Force transmission loss and force transmission accuracy are of particular concern for flexible instruments (such as endoluminal devices used for performing medical procedures) since the available force to actuate or otherwise apply at the end effector decreases exponentially with the coefficient of friction and the total bend angle that the actuator element travels around. When actuator elements such as control cables need to travel around a bend, pulleys are often used to reduce friction. Unfortunately, space isn't always available for pulleys, such as in a minimally invasive flexible instrument.

As an example of such a flexible instrument, a robotically manipulated endoluminal device may be employed that enters the patient through a single minimally invasive incision or through a body orifice, such as the mouth, rectum, vagina, or urethra, to reach a surgical or diagnostic site within a patient by passing, at least partially along with way, through a natural body lumen. The endoluminal device in this case may integrate surgical instruments and an image capturing device into one unit.

One application for such an endoluminal device is Natural-Orifice Transluminal Endoscopic Surgery ("NOTES"), which may involve, for example, passing flexible instruments through one of the body's orifices and entering the abdomen from the inside of the patient, rather than through a minimally invasive incision from the outside. Among the many technological challenges in building medical robotic systems for NOTES, the medical devices used in such systems need to be long, slender, flexible, and steerable to maneuver around bends inside the lumen. Moreover, the medical devices must be articulate and yet provide sufficient force and accuracy to carry out necessary tasks at the distal end. Given anatomy size limitations, all actuators (e.g., motors) used to drive control elements/links (e.g., cables, rods, gears, etc.) to provide the medical device's steerability and articulation must be located at the proximal end of the medical devices which is generally outside the patient. This means that the actuators must be able to produce enough torque to overcome a substantial amount of friction created when the control elements slide over or otherwise interact with surfaces as they travel around numerous bends in their respective medical devices.

To avoid the friction problems associated with actuator elements such as described above, hydraulic or other servo mechanisms may be used to control the end effector at the distal end of the instrument in lieu of actuator elements. The hydraulic cylinder at the distal end can be bulky, however, compared to direct cable actuation. Further, the hydraulic cylinder and seal have friction of its own to contend with.

Alternatively, large actuators (e.g., in a hydraulic system) may be used to overcome the sliding friction. Such large actuators, however, present their own challenges in terms of lack of precise movements and the large space they require given the number of motors that may be needed to provide the required Degrees of Freedom (DOF) in NOTES medical devices. Accordingly, large actuators are not generally desirable.

"Dithering" is a commonly used method for compensating for stiction. Applied in this case, oscillating forces with a peak approximately equal to the stiction would be applied to the actuator elements so that the actuator elements are prevented from ever being fully at rest. Dithering, however, may result in vibrations that are uncomfortable to the operator of an instrument employing the actuator elements and result in wear and tear on mechanical parts. "Coulomb" friction compensation is a commonly used method for compensating for Coulomb friction. Applied in this case, the direction of the velocity of an actuator element is sensed and a compensating force is applied to the actuator element according to the sensed velocity direction in order to compensate for the Coulomb friction. Since it is difficult to measure velocity accurately when the actuator element is at rest, however, due to measurement inaccuracies, noise, and the like, it is problematic in applying the compensating force in the correct direction.

OBJECTS AND SUMMARY OF THE INVENTION

Accordingly, one object of one or more aspects of the present invention is to reduce at least one friction force opposing an axial force exerted through an actuator element.

Another object of one or more aspects of the present invention is to reduce jerky stick-slip motion induced while actuating an end effector by an actuator element.

Another object of one or more aspects of the present invention is to effectively transfer applied forces through an actuating element to an end effector actuated by the actuating element.

Yet another object of one or more aspects of the present invention is to effect viscous motion when moving an actuator element in an axial direction.

Still another object of one or more aspects of the present invention is to controllably vary the viscosity of viscous motion effectuated when moving an actuator element in an axial direction.

These and additional objects are accomplished by the various aspects of the present invention, wherein briefly stated, one aspect is a method for reducing at least one friction force opposing a force exerted axially through an actuator element disposed within a housing, comprising: rotating one of the actuator element and the housing relative to the other, wherein the housing has an inner surface at least partially in physical contact with the actuator element during at least part of the time of such rotating.

Another aspect is an apparatus for reducing at least one friction force opposing a force exerted axially through a first actuator element, comprising: a first housing disposed around the first actuator element and having an inner surface at least partially in physical contact with the first actuator element; and a first actuator configured to rotate one of the first actuator element and the first housing relative to the other.

Additional objects, features and advantages of the various aspects of the present invention will become apparent from the following description of its preferred embodiment, which description should be taken in conjunction with the accompanying drawings.

DETAILED DESCRIPTION OF THE PREFERRED EMBODIMENT

In the following detailed description of the present invention, numerous specific details are set forth in order to provide a thorough understanding of the present invention. However, it will be obvious to one skilled in the art that the present invention may be practiced without these specific details. In other instances well known methods, procedures, components, and mechanisms have not been described in detail as not to unnecessarily obscure aspects of the present invention. While the following detailed description of the present invention is related to minimally invasive medical devices and/or guide tubes, it is to be appreciated that the present invention and its principles are also applicable to many other mechanical devices that have undesirable friction resulting from contact between moving parts.

Various instances and assemblies of flexible instruments and guide tubes are known. Such flexibility is achieved in various ways. For example, a segment of an instrument or guide tube may be a continuously curving flexible structure, such as one based on a helical wound coil or on tubes with various segments removed (e.g., kerf-type cuts). Alternatively, the flexible part may be made of a series of short, pivotally connected segments (e.g., "vertebrae") that provide a snake-like approximation of a continuously curving structure. Instrument and guide tube structures may include those in U.S. Patent Application Pub. No. US 2004/0138700 (Cooper et al.), which is incorporated herein by reference.

For clarity, the figures and associated descriptions may on occasion show only two segments of instruments and/or guide tubes, termed proximal (closer to the transmission mechanism; farther from the work site) and distal (farther from the transmission mechanism; closer to the work site). It should be understood that the instruments and guide tubes may be divided into three or more segments, each segment being rigid, passively flexible, or actively flexible. Flexing and bending as described for a distal segment, a proximal segment, or an entire mechanism also apply to intermediate segments that have been omitted for clarity. For instance, an intermediate segment between proximal and distal segments may bend in a simple or compound curve. Flexible segments may be various lengths. Segments with a smaller outside diameter may have a smaller minimum radius of curvature while bending than segments with a larger outside diameter.

For cable-controlled systems, unacceptably high cable friction or binding limits minimum radius of curvature and the total bend angle while bending. The guide tube's (or any joint's) minimum bend radius is such that it does not kink or otherwise inhibit the smooth motion of the inner surgical instrument's mechanism. The amount of friction is directly related to the amount of bending (e.g., total bending angle in a cable) which acts to decrease the amount of force available for actual work by the end effector at the distal end.

In some instances only a distal segment of an instrument or guide tube is flexible, and the proximal segment is rigid. In other instances, the entire segment of the instrument or guide tube that is inside the patient is flexible. In still other instances, an extreme distal segment may be rigid, and one or more other proximal segments are flexible. The flexible segments may be passive or they may be actively controllable (i.e., "steerable"). Such active control may be done using, for example, sets of opposing cables (e.g., one set controlling "pitch" and an orthogonal set controlling "yaw"; three cables can be used to perform similar action). In instances in which a segment of an instrument or guide tube is fully or partially inside another guide tube, various combinations of passive and active flexibility may exist. For instance, an actively flexible instrument inside a passively flexible guide tube may exert sufficient lateral force to flex the surrounding guide tube. Similarly, an actively flexible guide tube may flex a passively flexible instrument inside it. Actively flexible segments of guide tubes and instruments may work in concert. For both flexible and rigid instruments and guide tubes, control cables placed farther from the center longitudinal axis may provide a mechanical advantage over cables placed nearer to the center longitudinal axis, depending on compliance considerations in the various designs.

The flexible segment's stiffness may vary from being almost completely flaccid (small internal frictions exist) to being substantially rigid. In some aspects, the compliance is controllable. For example, a segment or all of a flexible segment of an instrument or guide tube can be made substantially (i.e., effectively but not infinitely) rigid (the segment is "rigidizable" or "lockable"). The lockable segment may be locked in a straight, simple curve or in a compound curve shape. Locking may be accomplished by applying tension to one or more cables that run longitudinally along the instrument or guide tube that is sufficient to cause friction to prevent adjacent vertebrae from moving. The cable or cables may run through a large, central hole in each vertebra or may run through smaller holes near the vertebra's outer circumference. Alternatively, the drive element of one or more motors that move one or more control cables may be soft-locked in position (e.g., by servocontrol) to hold the cables in position and thereby prevent instrument or guide tube movement, thus locking the vertebrae in place. Keeping a motor drive element in place may be done to effectively keep other movable instrument and guide tube components in place as well. It should be understood that the stiffness under servocontrol, although effective, is generally less than the stiffness that may be obtained with braking placed directly on joints, such as the braking used to keep passive setup joints in place. Cable stiffness generally dominates because it is generally less than servosystem or braked joint stiffness.

One example of an instrument that includes a mechanical device utilizing the various aspects of the present invention is an instrument employed in a medical robotic system such as a minimally invasive surgical system. Although the following description describes one embodiment of the invention, it is to be appreciated from the foregoing explanation that the invention may be used in many other forms and applications.

Figure 1:
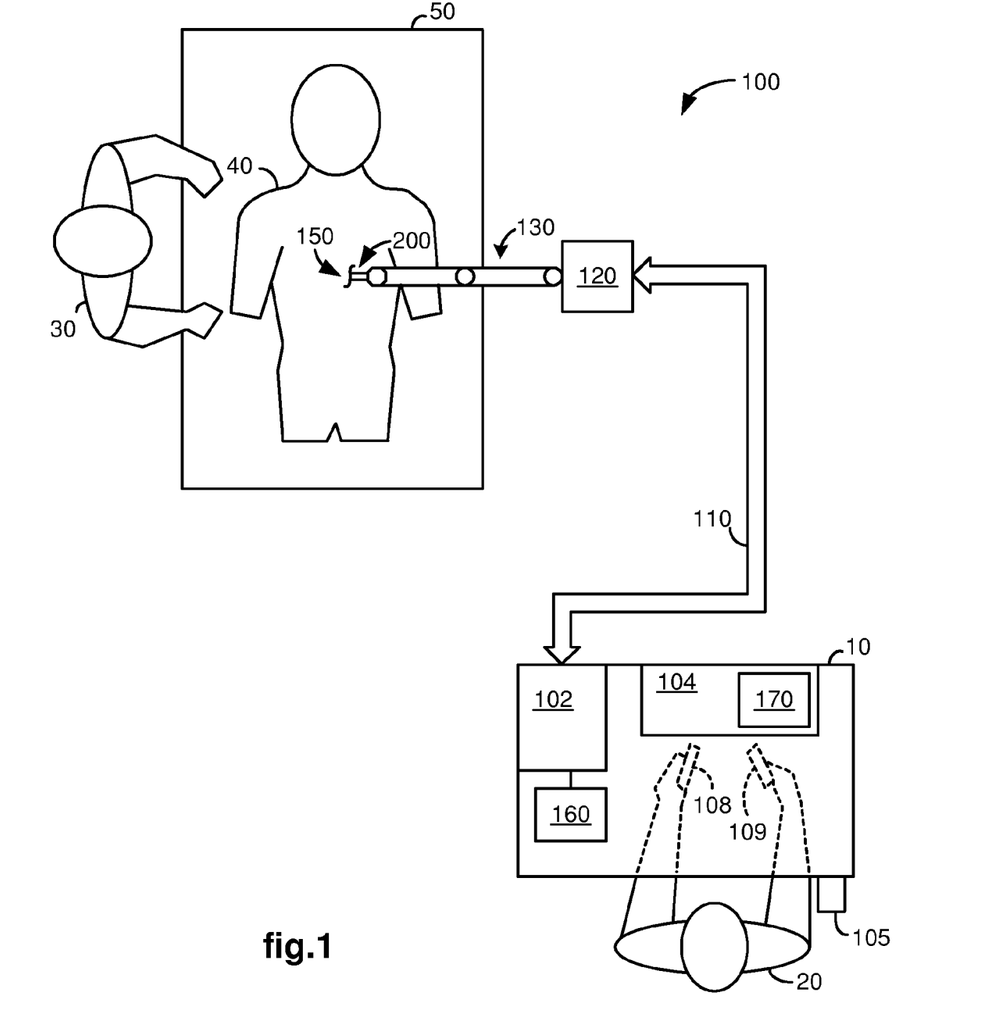
FIG. 1 illustrates a top view of an operating room employing a medical robotic system for manipulating an instrument in which aspects of the present invention may be utilized.

FIG. 1 illustrates, as an example, a top view of an operating room in which a medical robotic system 100 is being utilized by a Surgeon 20 for performing a medical procedure on a Patient 40 who is lying face up on an operating table 50. One or more Assistants 30 may be positioned near the Patient 40 to assist in the procedure while the Surgeon 20 performs the procedure teleoperatively by manipulating input devices 108, 109 on a surgeon console 10.

In the present example, an instrument 200 is inserted through a single entry port 150 into the Patient 40. Although the entry port 150 is a minimally invasive incision in the present example, in the performance of other medical procedures, it may instead be a natural body orifice. The instrument 200 is held and manipulated by a robotic arm assembly 130.

As with other parts of the medical robotic system 100, the illustration of the robotic arm assembly 130 is simplified in FIG. 1. In one example of the medical robotic system 100, the robotic arm assembly 130 includes a setup arm and an instrument manipulator. The setup arm is used to position the instrument 200 at the entry port 150 so that it properly enters the entry port 150. The instrument manipulator is then used to robotically insert and retract the instrument 200 into and out of the entry port 150. It may also be used to robotically pivot the instrument 200 in pitch, roll and yaw relative to a longitudinal axis of the instrument 200 about a pivot point located at the entry port 150.

The console 10 includes a 3-D monitor 104 for displaying a 3-D image of a surgical site to the Surgeon, left and right hand-manipulatable input devices 108, 109, a foot pedal 105, and a processor (also referred to herein as a "controller") 102. The input devices 108, 109 may include any one or more of a variety of input devices such as joysticks, gloves, trigger-guns, hand-operated controllers, or the like. Other input devices that are provided to allow the Surgeon to interact with the medical robotic system 100 include a foot pedal 105, a conventional voice recognition system 160 and a Graphical User Interface (GUI) 170.

The console 10 is usually located in the same room as the Patient so that the Surgeon may directly monitor the procedure, is physically available if necessary, and is able to speak to the Assistant(s) directly rather than over the telephone or other communication medium. However, it will be understood that the Surgeon can also be located in a different room, a completely different building, or other remote location from the Patient allowing for remote surgical procedures.

The processor 102 performs various functions in the system 100. One important function that it performs is to translate and transfer the mechanical motion of input devices 108, 109 through control signals over bus 110 so that the Surgeon can effectively manipulate and otherwise move devices, such as the instrument 200, that are selectively associated with the input devices 108, 109 at the time. Although only one instrument 200 is shown in FIG. 1, in practical application of the medical robotic system 100, three or more medical devices (such as two or more surgical tools and an image capturing device) may be employed. Each of the medical devices in such case may be deployed through its own entry port or bundled together through a single entry port by a guide tube or as part of an endoluminal device.

Although described as a processor, it is to be appreciated that the processor 102 may be implemented in practice by any combination of hardware, software and firmware. Also, its functions as described herein may be performed by one unit or divided up among different components, each of which may be implemented in turn by any combination of hardware, software and firmware. Further, although being shown as part of or being physically adjacent to the console 10, the processor 102 may also comprise a number of subunits distributed throughout the system.

For additional details on the construction and operation of general aspects of a medical robotic system such as described herein, see, e.g., U.S. Pat. No. 6,493,608 "Aspects of a Control System of a Minimally Invasive Surgical Apparatus," and U.S. Pat. No. 6,671,581 "Camera Referenced Control in a Minimally Invasive Surgical Apparatus," which are incorporated herein by reference.

Figure 2:
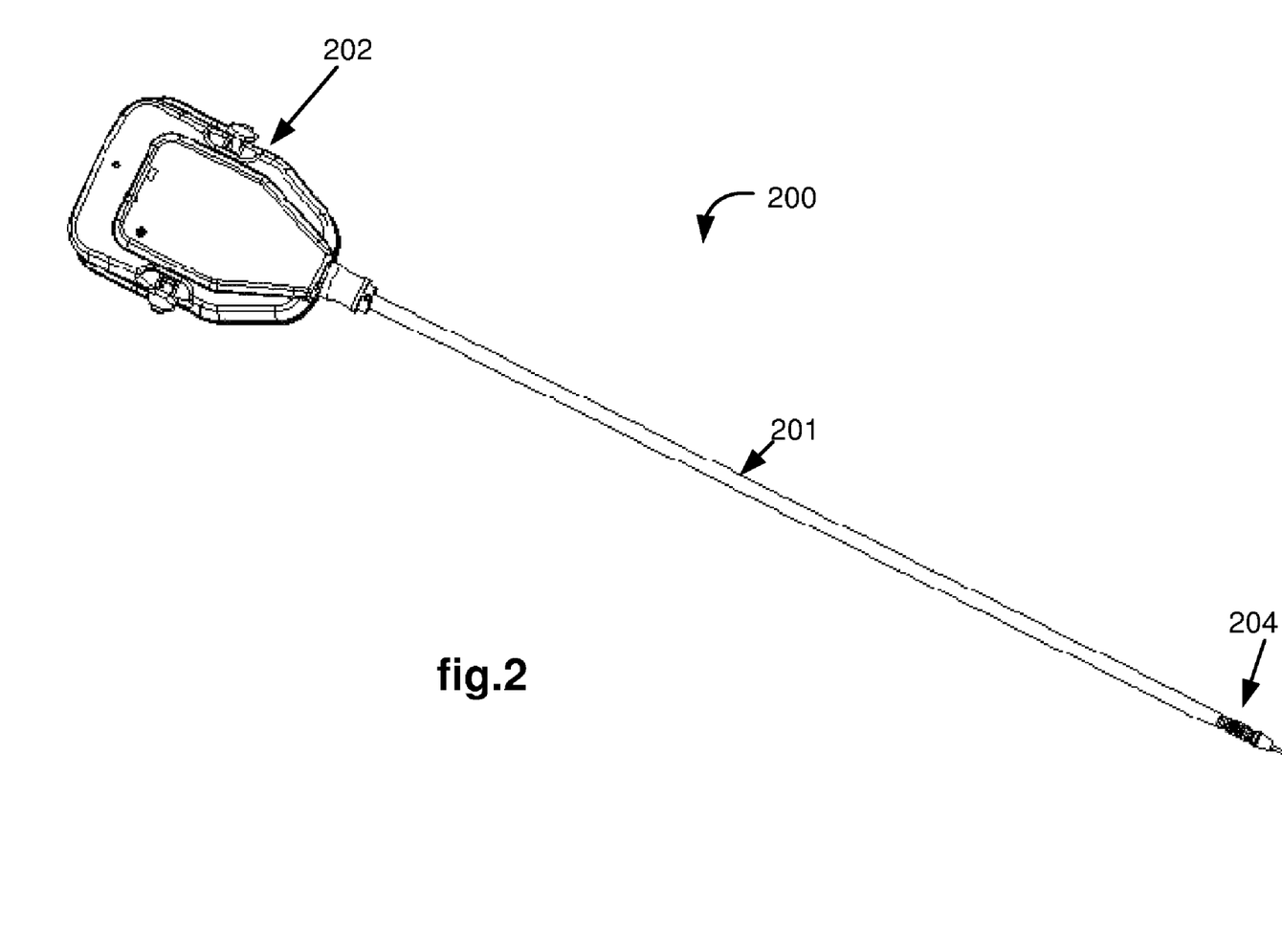
FIG. 2 illustrates a top view of an instrument in which aspects of the present invention may be utilized.

FIG. 2 illustrates, as an example, one embodiment of the instrument 200 that has an interface 202, a shaft 201 and an orientable tip 204. The interface 202 is mechanically coupled to actuators in the robotic arm 130 that respond to control signals generated by the processor 102 in response to operator manipulation of its associated input device. The orientable tip 204 is mechanically coupled to the interface 202 through actuator elements extending through the shaft 201 so that the tip 204 may be robotically controlled to bend in different directions in response to operator manipulation of an associated one of the input devices 108, 109. The shaft 201 (and each of the actuator elements) has a proximal end coupled to the interface 202, a distal end coupled to the orientable tip 204, and a longitudinal axis extending between the proximal and distal ends.

Figure 3:
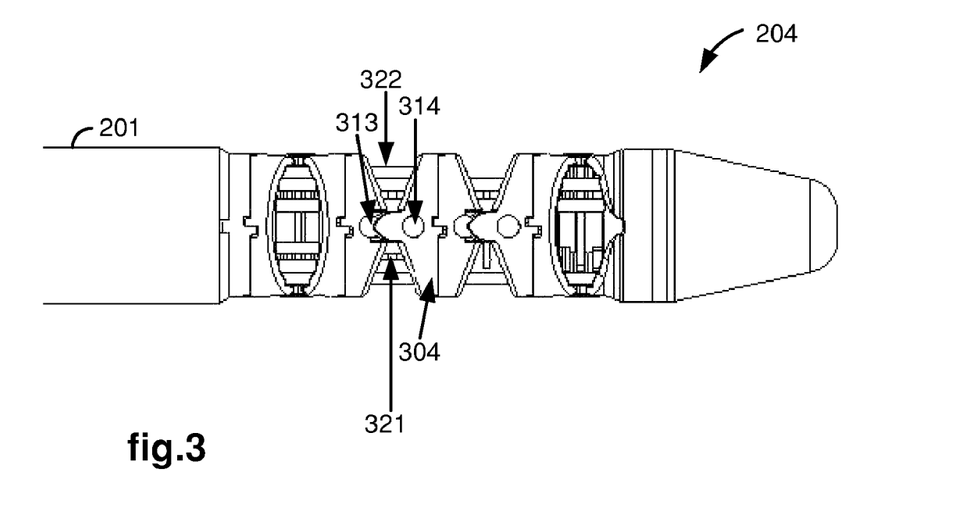
FIG. 3 illustrates a side view of a multi-jointed tip of an instrument in which aspects of the present invention may be utilized.

FIG. 3 illustrates, as an example, a four joint orientable tip 204 that is controllably orientable in pitch, roll and yaw angular directions relative to the longitudinal axis of the shaft 201 of the instrument 200. Four sections are shown, each comprising a pair of disk segments pivotably coupled together by an intervening strut. The first and fourth sections provide controllable yaw angular movement, and the second and third sections provide controllable pitch angular movement. The tip 204 is coupled to a distal end of the shaft 201 so that it rotates when the shaft 201 is rotated by its robotic arm 130 to provide controllable 360 degree roll angular movement.

Cables 321, 322 extend from a conventional motor driven pulley arrangement (not shown) in the interface 202 to disk segment 304 so that by pulling one or the other of the cables 321, 322, the disk segment 304 may be pivoted about pivots 313, 314 in one direction or the other. Similarly, other cable pairs (not shown) extend from other conventional motor driven pulley arrangements (not shown) in the interface 202 to their respective disk segments so that by pulling one or the other of the cables in the pair, the disk segment may be pivoted about its pivot joint in one direction or the other.

The dual pivots of each section of the tip 204 are coupled through the section's strut so that "cable balancing" is achieved wherein the cable length paid out on one side is equal to the cable length pulled on the other side of the disk segment. For additional details on such "cable balancing" and the construction and operation of the wrist mechanism of the orientable tip 204, as well as the construction and operation of other wrist mechanisms that may be alternatively used in the tip 204, see U.S. Pat. No. 6,817,974, "Surgical Tool having Positively Positionable Tendon-Actuated Multi-Disk Wrist Joint," which is incorporated herein by reference.

Although not shown in FIG. 3, an end effector may be attached to the distal end of the instrument 200 to perform a medical procedure. Examples of end effectors include graspers, scissors, forceps, clip appliers, scalpels, electrocautery probes, and retracters, to name a few. The end effector can be permanently attached or be removable and optionally replaceable with a different type of end effector depending on the medical need. A wrist mechanism such as shown in FIG. 3 may also be provided so that the end effector may be oriented as desired. Cables extending from the interface 202 to the end effector may be used in a conventional manner to actuate the end effector.

Although the actuator elements described in referenced to FIGS. 2-3 are cables, it is to be appreciated that other types of actuator elements performing the same function, such as push rods, may alternatively be used and are fully contemplated to be within the scope of the present invention.

Figure 4:
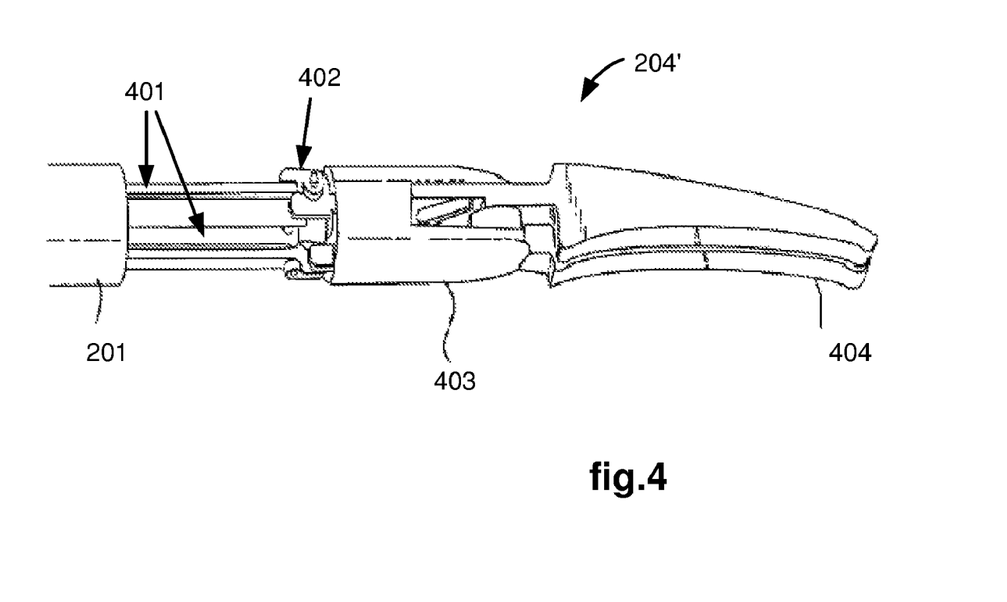
FIG. 4 illustrates a perspective view of an instrument in which aspects of the present invention may be utilized.

FIG. 4 illustrates, as an example, an end effector 204' which includes a distal clevis 403 and graspers 404 coupled to the distal clevis 403. Push rods 401 extend through the shaft 201 and are mechanically coupled at their proximal ends to the interface 202 of the instrument 200 and coupled at their distal ends to orthogonal linkages 402. The push rods 401 and orthogonal linkages 402 cooperate to serve as a wrist mechanism for controllably orienting the distal clevis 403 and consequently, the graspers 404 in pitch and yaw. One or more actuator elements (not shown) also extend through the shaft 201 (preferably in an area between push rods 401) and is/are mechanically coupled at its/their proximal end(s) to the interface 202 of the instrument 200 and coupled at its/their distal end(s) to one or both members of the graspers 404 to actuate the graspers 404 (i.e., cause them to open and close). Additional details on such push rod wrist mechanisms are described, for example, in U.S. Pat. No. 6,699,235, "Platform Link Wrist Mechanism," which is incorporated by reference.

The actuator elements (i.e., cables in FIG. 3 and push rods in FIG. 4) may interact with surfaces within the shaft 201 resulting in undesirable friction forces opposing axial forces exerted through the actuator elements (i.e., forces exerted along the longitudinal axes of the actuator elements such as a gripping force exerted by a user of an instrument on its handle that is to be transmitted through the actuator element as a push or pull force to an end effector of the instrument to grasp an object). To counteract such friction forces, each of the actuator elements is sheathed by a tubular housing and one of the actuator element and tubular housing is rotated relative to the other to reduce the effects of such friction forces. By rotating the tubular housing, for example, stiction between the housing and the actuator element is eliminated without the vibration problems encountered with "dithering." As will be explained further below, additional benefits over conventional friction reducing mechanisms are also realized by such rotation.

Figure 5:
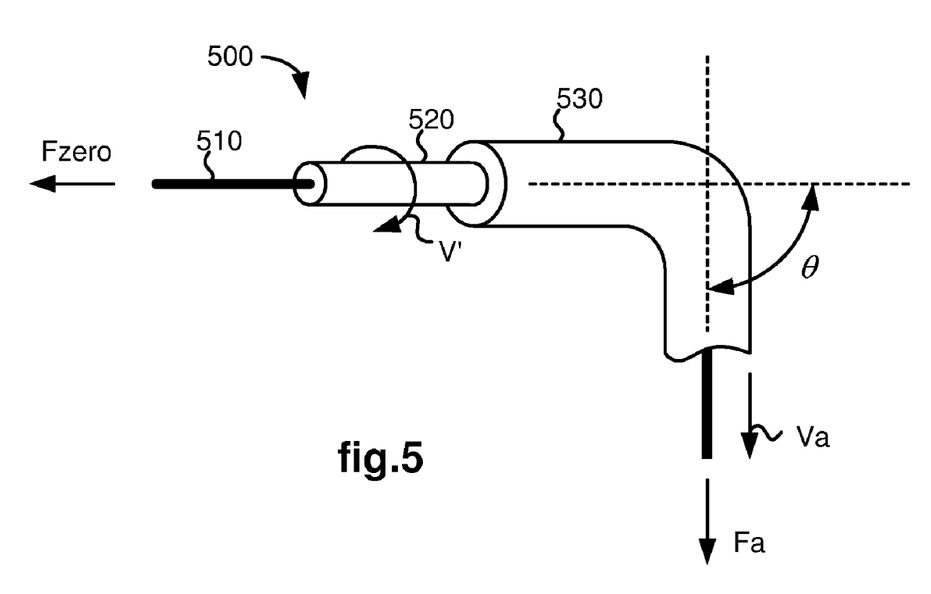
FIG. 5 illustrates a perspective view of a cut-out portion of a mechanical device utilizing aspects of the present invention.

FIG. 5 illustrates a perspective view of an actuator element 510, tubular housing 520, and outer housing 530. Although the actuator element 510 is shown extending out of the distal end of tubular housing 520 and the tubular housing 520 is shown extending out of the distal end of the outer housing 530 in this example, it is to be appreciated that such extensions are merely for illustrative purposes.

Figure 9:
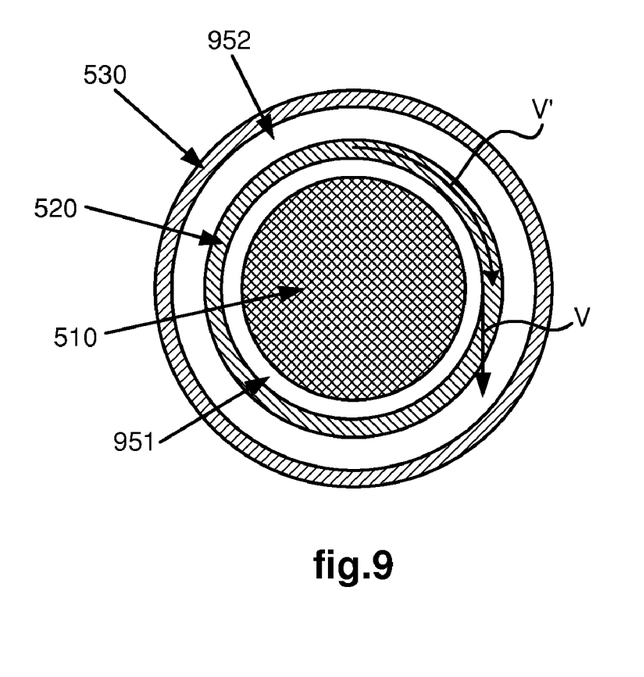
FIG. 9 illustrates a cross-sectional view of an actuator element and its housings in a mechanical device utilizing aspects of the present invention.

The actuator element 510 is movable in an axial direction along the longitudinal axis of the actuator element 510 (indicated by straight arrow Va) for actuating an end effector of an instrument or orienting a distal end of an instrument. The tubular housing 520 is axially rotatable about the longitudinal axis of the actuator element 510 (indicated by circular arrow V'). The outer housing 530 remains stationary while the actuator element 510 axially moves and the tubular housing 520 axially rotates. A cross-sectional view of the outer housing 530, tubular housing 520, and actuator element 510 is shown in FIG. 9. As shown in that figure, the rotational velocity V' of the tubular housing 520 results in a tangential velocity V. A lubricant 952 may be disposed between the tubular housing 520 and outer housing 530 to reduce friction between the two housings as the tubular housing 520 axially rotates. Lubricant 951 may also be disposed between the tubular housing 520 and the actuator element 510 to reduce friction between these two as either or both move relative to each other.

The outer housing 530, tubular housing 520, and actuator element 510 are each bent at an angle θ in FIG. 5. As previously explained such bending may be performed actively or passively. As a result of such bending, the steady-state force F0 (Fzero) experienced at the distal tip of the actuator element 510, which results from a force Fa provided at a proximal end of the actuator element 510 to move the actuator element 510 in the axial direction at a velocity Va, may be calculated using the following equation:

$$\frac{F_a}{F_0} = e^{\mu\theta \sin(\arctan(V_a/V))} \qquad (1)$$

where "V" is the tangential velocity of the axial rotation of the tubular housing 520, "$V_a$" is the velocity of the actuator element 510 in the axial direction, "μ" is the dynamic coefficient of friction between the actuator element 510 and the tubular housing 520, "$F_a$" is the actuation force being applied at the proximal end of the actuator element 510, "$F_0$" is the force resulting at the distal end of the actuator element 510, and "θ" is the total bend angle over the length of the actuator element 510. It is important to note that equation (1) is a steady-state equation that is only applicable as long as the magnitude of the tangential velocity V is greater than zero (i.e., either the tubular housing 520 is rotating relative to the actuator element 510 or vice versa). Also, since it is a steady-state equation, it does not take into account the propagation delay of the force Fa from one end of the cable to the other as the cable stretches or contracts when the force Fa is changed.

Figure 6A:
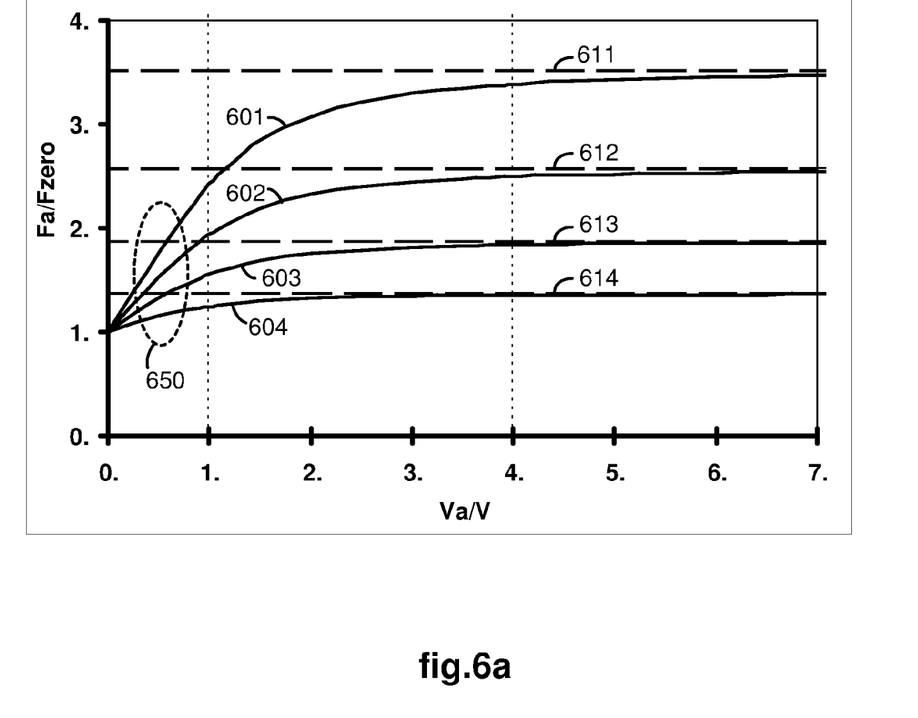
FIGS. 6a-6b illustrate force vs. velocity curves for a mechanical device utilizing aspects of the present invention.

FIG. 6a illustrates force ratio (Fa/F0) vs. velocity ratio (Va/V) curves 601-604 calculated using equation (1) for values of "μθ" ranging from 0.1 to 0.4 at 0.1 increments. Note that all curves exhibit viscous motion over their entire range. In other words, the slope of all curves is always positive. A shallow slope indicates a low viscosity in which the friction force Fa increases slowly with velocity Va (assuming V is fixed). A steep slope indicates a high viscosity in which the friction force Fa increases rapidly with velocity (such as in region 650). Viscous motion is good because it tends to be smooth and not jerky. For a given friction coefficient and wrap angle θ, the motion is more viscous at low speeds and it becomes less viscous at higher speeds.

When compared to a conventional actuator element and housing without axial rotation, the rotation of one of the housing or the actuator element relative to the other reduces the axial friction at all axial speeds. Dashed line force ratio (Fa/F0) vs. velocity (Va) curves 611-614 are shown in FIG. 6a (without showing "stiction" near zero velocity) for values of "μθ" corresponding to those of the force ratio (Fa/F0) vs. velocity ratio (Va/V) curves 601-604. As the tangential velocity V goes to zero, each of the curves 601-604 (with rotation) asymptotically approaches its corresponding one of the curves 611-614 (without rotation). At all velocities Va (for a given tangential velocity V), however, less proximal force Fa is required to generate a desired distal force F0 when rotation is employed (i.e., for each of the curves 601-604) as compared to when rotation is not employed (i.e., for corresponding ones of the curves 611-614). As an example, comparing the curve 601 (with rotation) with its corresponding curve 611 (without rotation), assuming a tangential velocity V of 1.0, at a velocity Va of 1.0 and a desired F0 of 1.0, it only takes an applied proximal force Fa of about 2.4 using curve 601 as compared to an applied proximal force Fa of about 3.5 using curve 611.

Figure 6B:
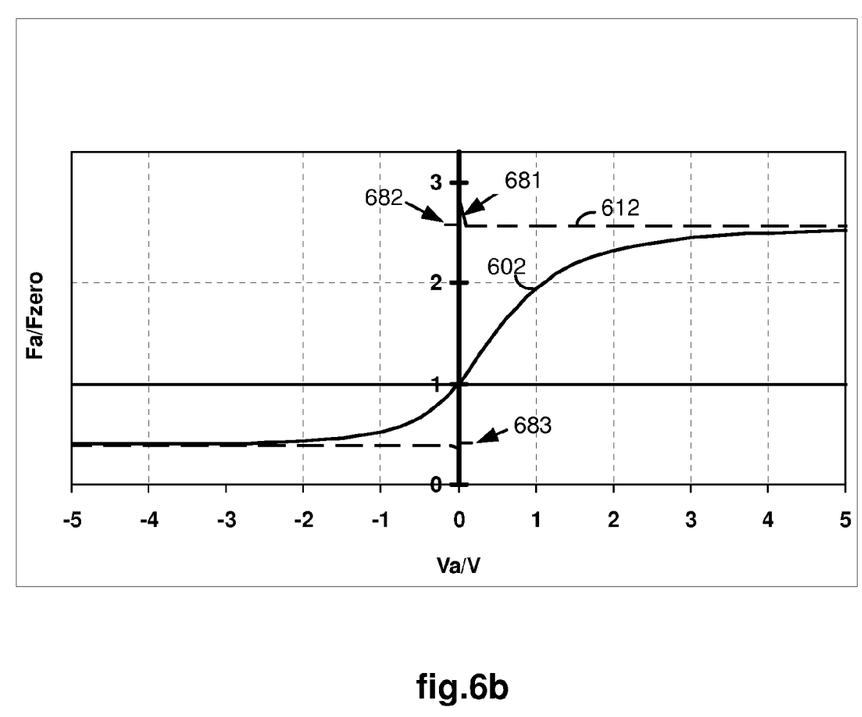

FIG. 6b illustrates the force ratio (Fa/F0) vs. velocity ratio (Va/V) curve 602 (with rotation) and its corresponding force ratio (Fa/F0) vs. velocity (Va) curve 612 (without rotation). Referring to the curve 612, two characteristics are noteworthy to point out. First, a "stiction" (static friction) region occurs on either side of the force axis. As previously mentioned, jerky, stick-slip motion can occur where the slope of the force vs. velocity curve is negative and such a negative slope occurs, for example, at the "stiction" region 681. Secondly, when a force F0 is desired to be held at the distal end of the actuating element 510 (such as a gripping force on an end effector actuated by the actuating element 510), it may be difficult to maintain the distal force, because the applied proximal force Fa may vary substantially (i.e., between points 682 and 683) while the velocity Va of the actuator element 510 is held around zero.

In contrast, the force ratio (Fa/F0) vs. velocity ratio (Va/V) curve 602 has a positive slope at all values. Thus, the rotational movement of the tubular housing 520 eliminates negative slopes so as to avoid jerky, stick-slip motion. Further, when the velocity Va of the actuator element 510 is zero, the force at the distal tip of the actuator element 510 is equal to the applied proximal force (i.e., at Va=0, F0=Fa), making it much easier to accurately hold a desired force F0 at the distal end of the actuator element 510.

To control the viscosity and force transmission efficiency of the actuator element 510, the tangential velocity V of the tubular housing 520 may be changed independently from Fa, Va and F0. In particular, the viscosity may be increased (i.e., the slope of the force vs. velocity curve increased) and the force transmission efficiency (i.e., Fzero/Fa) increased by increasing the tangential velocity V and the viscosity may be reduced (i.e., the slope of the force vs. velocity curve decreased) and the force transmission efficiency reduced by reducing the tangential velocity V. Thus, at high tangential velocities V, the movement of the actuator element 510 becomes very viscous so that the corresponding movement of the distal end of the actuator element 510 is smooth (i.e., eliminating jerky stick-slip motion) and the force F0 at the distal end of the actuator element 510 is closer to the force Fa at the proximal end of the actuator element 510 (i.e., the force ratio Fa/F0 is closer to 1.0).

Note that although pull forces are shown in FIGS. 6a and 6b, such as would be the case with cable actuator elements, the description and equations above are also applicable for push forces in the opposite direction than those shown, such as would be the case with push rod actuator elements.

Figure 7:
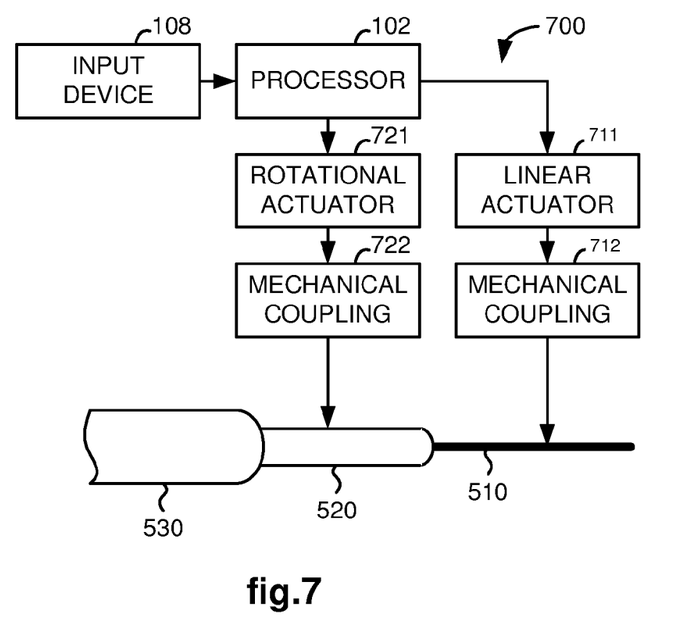
FIG. 7 illustrates a block diagram of a portion of a first embodiment of a friction countering mechanism used in a mechanical device utilizing aspects of the present invention.

FIG. 7 illustrates, as an example, a block diagram of a first embodiment 700 of the friction countering mechanism that operates at a proximal end of the actuator element 510 to controllably move the actuator element 510 in the axial direction at the velocity Va and controllably rotate the tubular housing 520 about the actuator element 510 at the tangential velocity V. As an example of using the friction countering mechanism, when the Surgeon desires to actuate the end effector of an instrument, the Surgeon manipulates the input device associated with the instrument. Sensed movement of the input device is then provided to a control system implemented in the processor 102, which generates appropriate actuator commands for actuating one or more actuator elements in the instrument for effectuating the desired actuation of the instrument. The actuator command for the actuator element 510, in this case, is provided to a linear actuator 711 which causes the actuator element 510 to apply a force Fa through the actuator element 510 with or without moving the actuator element 510 in the axial direction at the velocity Va through mechanical coupling 712. To reduce friction in the axial direction as described above, the processor 102 also generates an appropriate actuator command which it provides to a rotational actuator 721, which in turn, causes the tubular housing 520 to be axially rotated about the actuator element 510 at the tangential velocity V through mechanical coupling 722. Rotation of the tubular housing 520 is preferably performed prior to or simultaneously with the movement of the actuator element 510. To prevent the actuator element 510 from rotating with the tubular housing 520, the mechanical coupling 712 is configured to inhibit such rotation of the actuator element 510. Although separate actuators 711, 721 are shown as the preferred embodiment in this example (so that the rotational actuator 721 may be actuated before the linear actuator 711), only one actuator may be used if such rotational and linear motions are to be initiated simultaneously or if a delay element is provided so that the linear motion occurs after the rotational.

Figure 8:
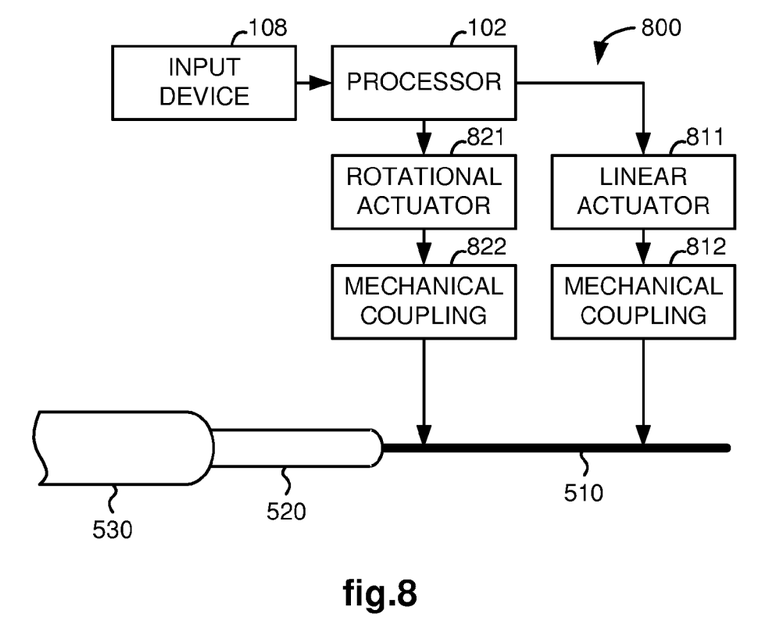
FIG. 8 illustrates a block diagram of a portion of a second embodiment of a friction countering mechanism used in a mechanical device utilizing aspects of the present invention.

FIG. 8 illustrates, as an example, a block diagram of a second embodiment 800 of the friction countering mechanism that operates at a proximal end of the actuator element 510 to controllably apply a force Fa through the actuator element 510 with or without moving the actuator element 510 in the axial direction at the velocity Va (using linear actuator 811 and mechanical coupling 812 at its proximal end) as well as controllably rotate the actuator element 510 at the tangential velocity V (using rotational actuator 821 and mechanical coupling 822 at its proximal end with a rotary coupling or bearing at its distal end). The tubular housing 520 in this embodiment remains stationary relative to the actuator element 510. As with the first embodiment, rotation of the actuator element 510 is preferably performed prior to or simultaneously with the movement of the actuator element 510 in the axial direction. Although separate actuators 811, 821 are shown as the preferred embodiment in this example (so that the rotational actuator 821 may be actuated before the linear actuator 811), only one actuator may be used if such rotational and linear motions are to be initiated simultaneously or if a delay element is provided so that the linear motion occurs after the rotational.

Figure 10:
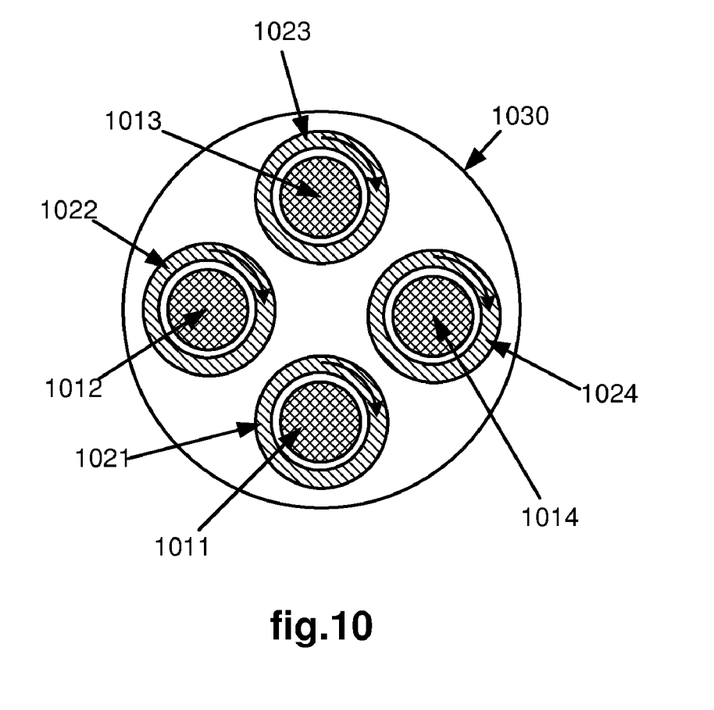
FIG. 10 illustrates a cross-sectional view of a mechanical device with a plurality of actuator elements and their respective tubular housings, utilizing aspects of the present invention.

Although a friction countering mechanism has been described for only one actuator element, actuation of an end effector and/or orienting the distal end of an instrument may require that more than one actuator element be moved in an axial direction at the same time. Further, effectuating different actions may require the movement of different actuator elements. For example, moving a distal end of an instrument (or guide tube) in pitch generally requires movement of different actuator elements than moving the distal end in yaw. To accommodate such a multiple actuator element system, FIG. 10 illustrates a cross-sectional view of an instrument 1030 in which a plurality of actuator elements 1011-1014 extend through corresponding ones of a plurality of rotatable tubular housings 1021-1024. Each of the actuator elements 1011-1014 may be moved in the axial direction in the same manner as described in reference to the actuator element 510 and each of the tubular housings 1021-1024 may be axially rotated in the same manner as described in reference to the tubular housing 520. For economy of resources, all of the tubular housings 1021-1024 may be rotated using a common actuator. Alternatively, the tubular housings 1021-1024 may remain stationary while the actuator elements 1011-1014 are moved in the axial direction and axially rotated as described in reference to FIG. 8.

Although the various aspects of the present invention have been described with respect to one or more preferred embodiments, it will be understood that the invention is entitled to full protection within the full scope of the appended claims.

What is claimed is:

1. A robotic system comprising:
   an instrument having an end effector, a first actuator element coupled to the end effector, and a first housing through which the first actuator element extends while in physical contact with an inner surface of the first housing;
   at least one actuator mechanically coupled to at least one of the first actuator element and the first housing; and
   a processor configured to command the at least one actuator to provide relative rotational motion between the first actuator element and the first housing about a longitudinal axis of the actuator element when the first actuator element is moving in a first axial direction along the longitudinal axis of the first actuator element.

2. The robotic system according to claim 1, wherein the first actuator element comprises a cable and the first housing is tubular in shape.

3. The robotic system according to claim 1, wherein the first actuator element comprises a push rod and the first housing is tubular in shape.

4. The robotic system according to claim 1, wherein the processor is configured to command the at least one actuator to provide the relative rotational motion between the first actuator element and the first housing at a tangential velocity of the axial rotation that is greater than a moving velocity of the first actuator element in the first axial direction.

5. The robotic system according to claim 1, wherein the end effector has a first movable member, and wherein an axial force exerted through the first actuator element results in a force being applied by the first movable member when the first actuator element is actuating the end effector.

6. The robotic system according to claim 5, wherein the first movable member comprises a gripping member.

7. The robotic system according to claim 5, wherein the first movable member comprises a cutting member.

8. The robotic system according to claim 5, wherein the instrument has a shaft through which the first housing extends, wherein the first movable member of the end effector is coupled to the first actuator element at a distal end of the shaft, and wherein the at least one actuator includes a linear actuator that is mechanically coupled to the first actuator element at a proximal end of the shaft.

9. The robotic system according to claim 8, wherein the at least one actuator includes a rotary actuator that is mechanically coupled to the first housing at the proximal end of the shaft for rotating the first housing relative to the first actuator element.

10. The robotic system according to claim 8, wherein the at least one actuator includes a rotary actuator that is mechanically coupled to the first actuator element at the proximal end of the shaft for rotating the first actuator element relative to the first housing.

11. The robotic system according to claim 8, wherein the shaft, the first housing, and the first actuator element are flexible.

12. The robotic system according to claim 1, wherein the instrument has a second actuator element coupled to the end effector, wherein the instrument has a second housing through which the second actuator element extends while in physical contact with an inner surface of the second housing, and wherein the processor is configured to command the at least one actuator to provide relative rotational motion between the second actuator element and the second housing about a longitudinal axis of the second actuator element at least while the second actuator element is moving in a second axial direction along a longitudinal axis of the second actuator element.

13. The robotic system according to claim 12, wherein the processor commands the at least one actuator to provide the relative rotational motion between the second actuator element and the second housing at a tangential velocity of the axial rotation that is greater than a moving velocity of the second actuator element in the second axial direction.

14. The robotic system according to clam 13, wherein the at least one actuator is configured to inhibit rotation of the first and second actuator elements respectively about the longitudinal axes of the first and second actuator elements.

15. The robotic system according to claim 1, further comprising:
an input device;
wherein the processor is configured to command the at least one actuator to actuate the end effector in response to user manipulation of the input device by commanding the at least one actuator to move the first actuator element in the first axial direction.

16. The robotic system according to claim 1, wherein the instrument has a friction reducing element disposed between the first housing and the first actuator element.

17. The robotic system according to claim 16, wherein the friction reducing element comprises a lubricant material.

* * * * *